United States Patent
Faict et al.

[11] Patent Number: 5,925,011
[45] Date of Patent: *Jul. 20, 1999

[54] SYSTEM AND METHOD FOR PROVIDING STERILE FLUIDS FOR ADMIXED SOLUTIONS IN AUTOMATED PERITONEAL DIALYSIS

[75] Inventors: Dirk Faict, Assenede, Belgium; Chi J. Chen, Hawthorn Woods, Ill.; Francesco Peluso, Heverlee, Belgium; Robert Warren Childers, New Port Richie, Fla.; Patrick Balteau, Jambes; Vital Eerlingen, Leuven, both of Belgium; Paul Frederick Emerson, St. Louis Park, Minn.; Lisa Colleran, Arlington Heights, Ill.

[73] Assignee: Baxter International Inc., Deerfield, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/520,805
[22] Filed: Oct. 10, 1995
[51] Int. Cl.⁶ .................................................. A61M 1/00
[52] U.S. Cl. .............................. 604/29; 604/56; 604/82; 604/83; 222/145.5
[58] Field of Search ............................... 604/29, 80–83, 604/56; 222/145.5–145.6

[56] References Cited

U.S. PATENT DOCUMENTS

| | | | |
|---|---|---|---|
| 4,338,190 | 7/1982 | Kraus et al. | 604/29 |
| 4,586,920 | 5/1986 | Peabody | 604/29 |
| 4,618,343 | 10/1986 | Polaschegg | 604/29 |
| 5,091,094 | 2/1992 | Veech | 210/647 |
| 5,261,876 | 11/1993 | Popovich et al. | 604/29 |
| 5,344,392 | 9/1994 | Senninger et al. | 604/29 |

FOREIGN PATENT DOCUMENTS

| | | |
|---|---|---|
| 0 013 334 A2 | 7/1980 | European Pat. Off. . |
| 0 121 085 A1 | 10/1984 | European Pat. Off. . |
| 0650739 | 5/1995 | European Pat. Off. . |
| 2135598 | 9/1984 | United Kingdom . |
| 9211046 | 7/1992 | WIPO . |

OTHER PUBLICATIONS

Boen, S.T. et al. "Periodic Peritoneal Dialysis in the Management of Chronic Uremia" in *Trans. ASAIO,* vol. 8: 1962, pp. 256–265.

Kablitz, M.D. Carl et al. "Technological Augmentation of Peritoneal Urea Clearance: Past, Present and Future" in *Dialysis and Transplantation,* vol. 9, 1980, pp. 741–778.

Keshaviah, P. "On–Line Proportioning Systems" in *Clinical Dialysis,* 1995, pp. 68–69. Specifically, see Figures 3–4 on p. 68.

Maxwell, M.H. et al. "Peritoneal Dialysis" in *JAMA,* vol. 170, No. 8, 1959, pp. 917–921.

*Primary Examiner*—Mark Bockelman
*Attorney, Agent, or Firm*—Charles R. Mattenson; Thomas S. Borecki; Robert M. Barrett

[57] ABSTRACT

A system and a method are provided for admixing solutions. The system includes containers separately accessible by one or more pumps for mixture of the solutions in a container immediately before administration to a peritoneal cavity of a patient. Alternatively, the system and method allow for direct administration of the mixed solution to the peritoneal cavity of a patient without intermediate mixing thereof. The solutions may be mixed in predetermined ratios as input to the system prior to delivery.

25 Claims, 7 Drawing Sheets

SYSTEM AND METHOD FOR PROVIDING STERILE FLUIDS FOR ADMIXED SOLUTIONS IN AUTOMATED PERITONEAL DIALYSIS

BACKGROUND OF THE INVENTION

The present invention generally relates to a system and a method for mixing solutions. More specifically, the present invention relates to a system and method for admixed solutions for use in automated peritoneal dialysis (APD).

It is known that a number of different products are housed in containers prior to administration to a patient. For example, in the medical field, it is generally known that enteral, intravenous and peritoneal solutions may be housed in containers. Generally, medical solutions can be administered directly to a patient.

Often, one or more solutions or ingredients must be combined to form another solution to be administered to a patient. Combined medical solutions, however, may typically be unstable. Degradation of mixed solutions can occur during the manufacturing process, for example, during sterilization. Likewise, during long-term storage, such products may degrade or suffer reduced efficacy. For example, amino acid and dextrose may be combined to form a parenteral solution for intravenous administration to a patient. If amino acids and dextrose are combined in a single container and stored, discoloration often takes place. Other examples of incompatible solutions include: bicarbonate-dextrose; amino acid polymers-dextrose; bicarbonate-dextrose polymers; and amino acid polymers-dextrose polymers.

In view of the foregoing, in some situations, amino acids and dextrose are sold separately. If a combined amino acid and dextrose solution is prescribed, the amino acid solution and dextrose solution must be combined from two separate containers. The transfer of fluid from one container to another can, however, be time-consuming. Further, fluid transfer is often dangerous due to touch or airborne microbial contamination that may occur during the process.

Therefore, containers have been developed to provide a simplified and less time-consuming procedure for combining at least two solutions. For example, containers having more than one chamber for storing a respective number of solutions prior to mixing are known. The chambers of these containers are segregated from each other, but selective communication is possible through the use of a frangible seal or closure between the chambers which may be opened from outside the container by manipulating the walls of the container. However, often multiple fluids must be mixed.

And, often, different combinations of fluids require mixing, or only a single fluid is required for direct infusion to a patient, particularly patients undergoing automated peritoneal dialysis treatment.

In an APD system, it is often desirable to pump PD solutions from different containers in an alternate or simultaneous mode to obtain a mixture of APD solutions for direct delivery to a patient or intermediate delivery to a container for mixing and subsequent delivery to a patient. Further, the volumes of solutions used in APD are larger than volumes of solutions used in, for example, continuous ambulatory peritoneal dialysis (CAPD). Therefore, the ability to directly and simultaneously mix solutions prior to delivery or during delivery of solution to a patient undergoing APD is desirable.

A need, therefore, exists for an improved system and method for mixing solutions, particularly for mixing prior to administration or during administration to a patient undergoing automated peritoneal dialysis.

SUMMARY OF THE INVENTION

The present invention relates to a system and a method for mixing a solution for delivery to a patient. More specifically, the present invention relates to a system and a method for mixing fluids for delivery to a patient undergoing peritoneal dialysis.

In an embodiment, a system is provided for mixing a solution for delivery to a patient. The system comprises a first container holding a first fluid and a second container holding a second fluid. Means for mixing the first fluid and the second fluid is provided to form the solution wherein the first fluid and the second fluid are independently withdrawn from the first container and the second container, respectively. Means for delivery of the solution to the patient are further provided.

In an embodiment, the system has a control means monitoring the solution delivered to the patient. The control means is capable of controlling volume of the solution delivered to the patient.

In an embodiment, means are provided for heating the solution prior to delivery to the patient.

In an embodiment, the means for mixing includes a pump.

In an embodiment, the means for mixing includes a plurality of pumps.

In an embodiment, the first fluid and the second fluid are sterile.

In an embodiment, the solution is delivered to a patient undergoing peritoneal dialysis.

In another embodiment of the present invention, a method is provided for mixing fluids during delivery to a patient. The method comprises the steps of: providing a first container holding a first fluid, providing a second container holding a second fluid; withdrawing the first fluid and the second fluid from their respective containers sequentially or, alternatively, simultaneously; mixing the first fluid and the second fluid forming a mixed solution; and delivering the mixed solution to the patient.

In an embodiment, the method further comprises the step of controlling volume of withdrawal of the first fluid and the second fluid independently.

In an embodiment, the method further comprises the step of controlling volume of delivery of the mixed solution to the patient.

In an embodiment, the method further comprises the step of heating the mixed solution prior to delivery to the patient.

In an embodiment, the method is performed on a patient undergoing peritoneal dialysis.

In another embodiment of the present invention, a method is provided for direct infusion of a plurality of fluids to a patient. The method comprises the steps of: providing at least one container; filling the at least one container with the first one of the plurality of fluids; pumping the first one of the plurality of fluids to the patient; filling at least one container with the second one of the plurality of fluids; and pumping the second one of the plurality of fluids to the patient.

In an embodiment, the method further comprises the step of inputting an amount of each of the plurality of fluids to be pumped to the patient.

In another embodiment of the present invention, a method is provided for direct and simultaneous infusion of a plurality of fluids to a patient. The method comprises the steps of: providing a plurality of containers equal to the plurality of fluids; and pumping each of the plurality of fluids from each of the plurality of containers simultaneously to the patient.

In an embodiment, the method further comprises the step of inputting an amount of each of the plurality of fluids to be pumped to the patient.

In another embodiment of the present invention, a system is provided for infusion of a plurality of solutions to a patient. The system has a means for storing each of the plurality of solutions and an input means for inputting an amount of each of the plurality of solutions required for delivery to the patient. A pumping means is capable of pumping each of the plurality of solutions to the patient.

In an embodiment, the pumping means simultaneously pumps each of the solutions to the patient.

In an embodiment, the pumping means sequentially pumps each of the solutions to the patient.

In an embodiment, the pumping means alternately pumps each of the solutions to the patient.

In an embodiment, storage means is provided for receiving each of the plurality of solutions for mixing prior to delivery to the patient.

In an embodiment, control means are provided and is operatively connected to the pumping means and is capable of controlling the pumping means for sequential or simultaneous delivery of the solution.

In an embodiment, means are provided for heating at least one of the plurality of solutions.

It is, therefore, an advantage of the present invention to provide a system and a method for admixing solutions for peritoneal dialysis.

Another advantage of the present invention is to provide a system and a method for admixing solutions for automated peritoneal dialysis (APD).

Yet another advantage of the present invention is to provide a system and a method to mix two or more solutions to obtain a ready-to-use solution for APD.

A still further advantage of the present invention is to provide a system and a method for providing solutions to a patient containing ingredients which cannot be sterilized together.

Further, an advantage of the present invention is to provide a system and a method for active mixing of fluids prior to administration to a patient.

And, another advantage of the present invention is to provide a system and a method for direct infusion of different fluids into a patient.

Moreover, an advantage of the present invention is to provide a system and a method for monitoring and controlling predetermined ratios of fluids for direct infusion into a patient or via mixing of the predetermined ratios of solutions prior to delivery.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a system and a method for mixing solutions. More specifically, the present invention provides a system and a method for mixing solutions for use in automated peritoneal dialysis (APD) and administration of the solutions to a patient.

Figure 1:
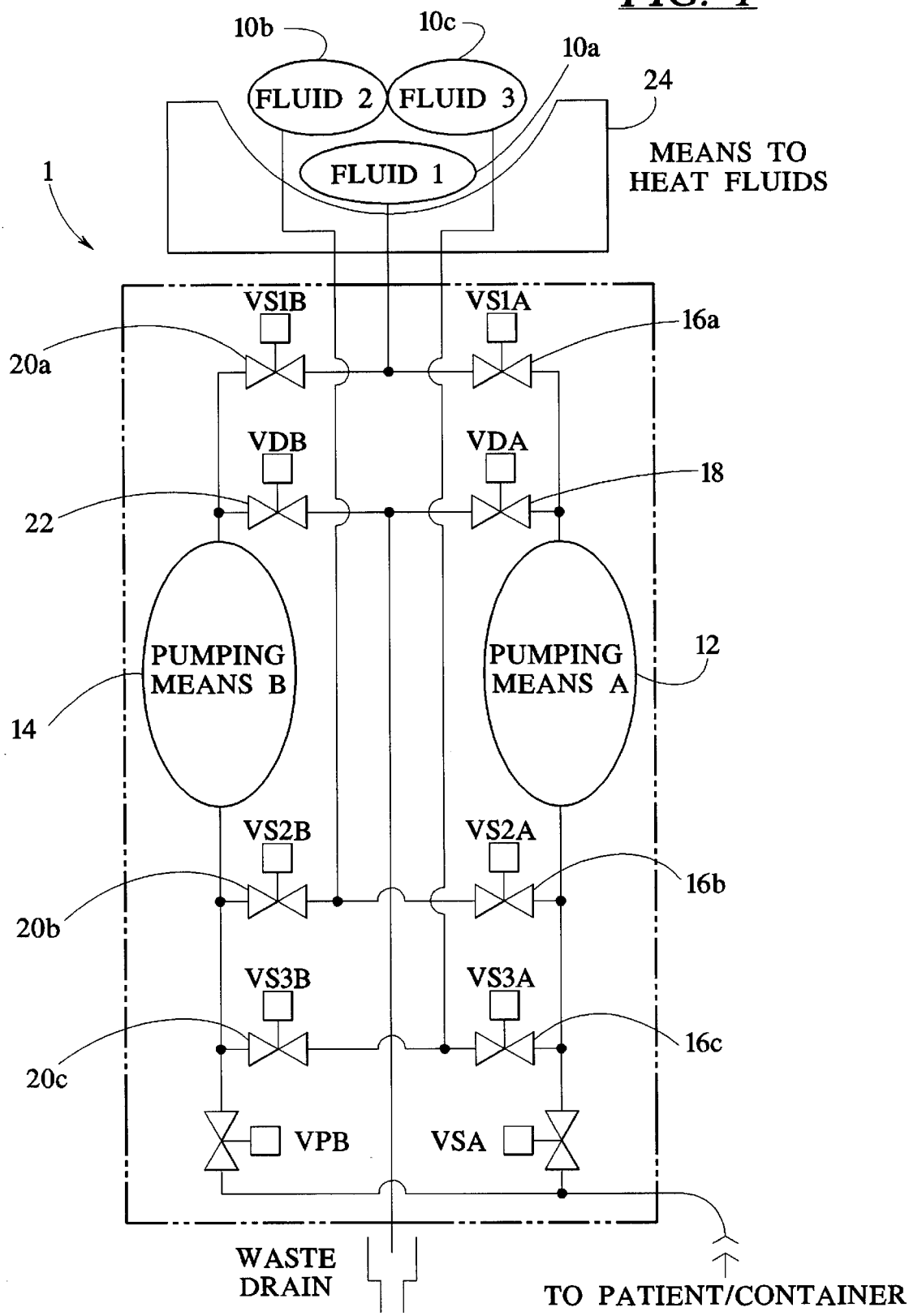
FIG. 1 illustrates a schematic diagram of an embodiment of a system for pumping multiple components of the present invention.

Referring now to FIG. 1, an embodiment of a system 1 for active mixing of a plurality of components is illustrated. In the embodiment of the system 1 illustrated, three fluid containers 10a, 10b and 10c are shown. The containers 10a, 10b and 10c hold three separate fluids or components required to be mixed prior to delivery to a patient. Although three containers 10a, 10b and 10c are shown, only two of the three containers may contain components required to be administered to a patient. Alternatively, a single one of the components may be delivered to a patient without mixing. As should be understood, any type of container such as a bag, a vial or the like, may be implemented. Container should, therefore, not be deemed as limiting, but rather as any source capable of holding a fluid or other component.

As illustrated, two pumps 12 and 14 are illustrated in the system 1. The pumps 12 and 14 are operatively connected to supply valves. The first pump 12 controls pumping of fluids through supply valves 16a, 16b and 16c, as well as drain valve 18. The pump 14 controls pumping through supply valves 20a, 20b and 20c, as well as drain valve 22. Therefore, each of the pumps 12, 14 can access the supply valves associated with each fluid in the fluid containers 10a, 10b and 10c. This permits mixing of all of the solutions from the fluid containers 10a, 10b and 10c in a real time mode.

In an embodiment of the present invention, the fluid in the fluid containers 10a, 10b, and 10c are sterile fluids requiring separate storage thereof. The fluids may be actively and aseptically mixed while being delivered to a patient undergoing peritoneal dialysis. The pumps 12 and 14 operate independently and deliver a resultant fluid mixture to a patient at a controlled rate until a desired amount of fluid has been delivered to the patient.

As illustrated, a heater 24 may also be provided to heat the fluids in the containers 10a, 10b and 10c. Alternatively, the fluids may be heated in line prior to administration to a patient.

Figure 2:
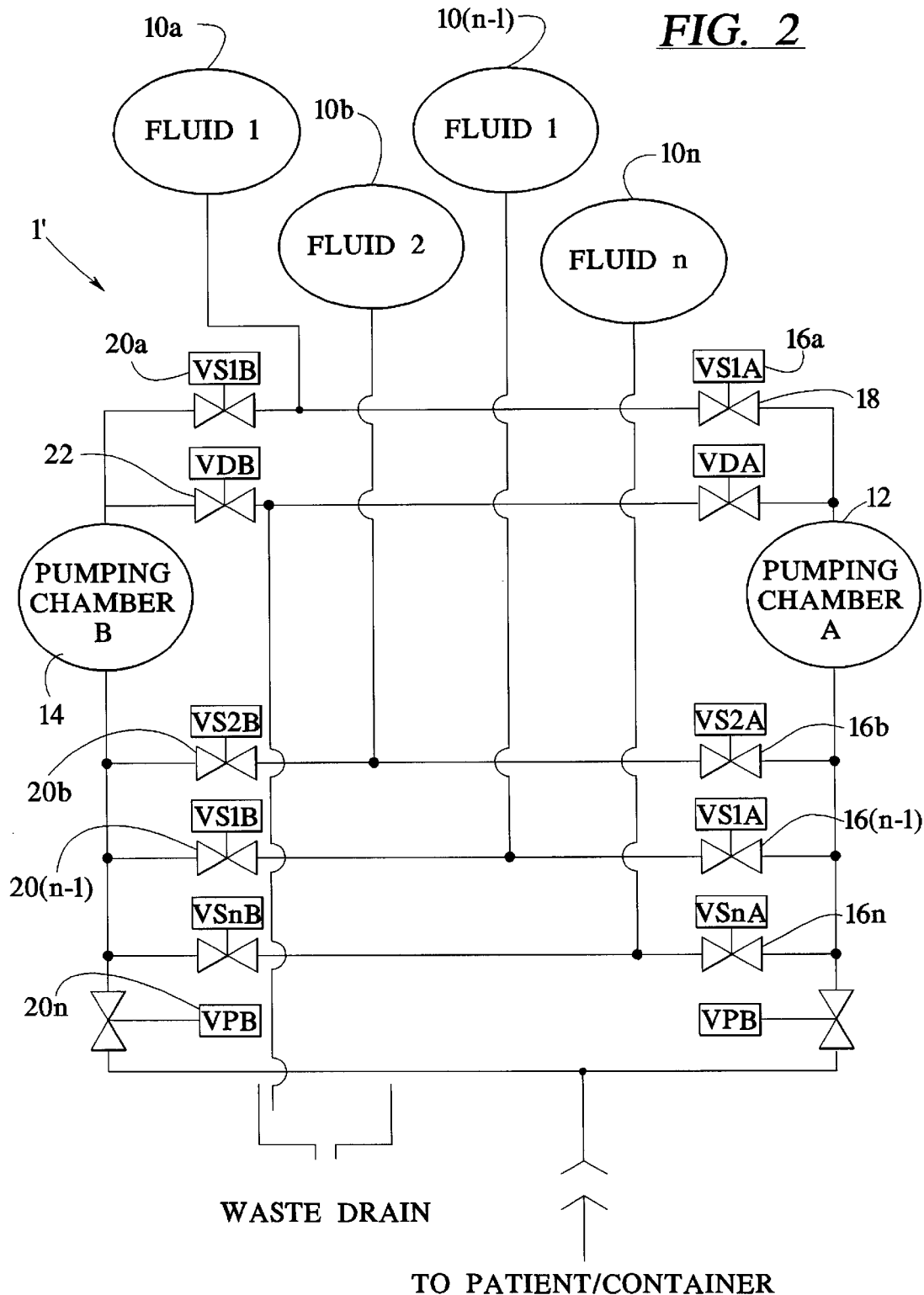
FIG. 2 illustrates a schematic diagram of another embodiment of a system of the present invention for pumping a plurality of components.

Another embodiment of the present invention is illustrated in FIG. 2. In the embodiment illustrated, fluid containers 10a, 10b . . . 10(n−1) and 10n are shown. An equal number of supply valves 16a, 16b . . . 16(n−1), 16n are shown and are controlled and accessible by a pump 12. Likewise, a second pump 14 controls and accesses an equal number of supply valves 20a, 20b . . . 20(n−1) and 20n. Drain valves 18 and 22 are also controllable and accessible by the pumps 12 and 14, respectively.

As illustrated in FIGS. 1 and 2, the systems 1 shown illustrate pumping of solutions to a patient or an intermediate container for mixing therein prior to pumping to the patient. In addition, a waste drain is provided for draining solution from containers in the system 1 or merely draining from conduit running through the system 1 including the valves and pumps. Further, while two pumping chambers 12 and 14 are illustrated, additional pumping chambers may be implemented by those skilled in the art. The system 1 is, therefore, designed for active mixing and pumping of parenteral dialysis solutions from different containers in alternate or simultaneous modes to obtain a mixture of PD solutions for ultimate delivery to a patient.

Two options for active mixing are available: a) a first option prepares a mixture of fluids in an intermediate container before administration to a patient; and b) a second option directly infuses fluids from different containers into a peritoneal cavity of a patient.

Figure 3:
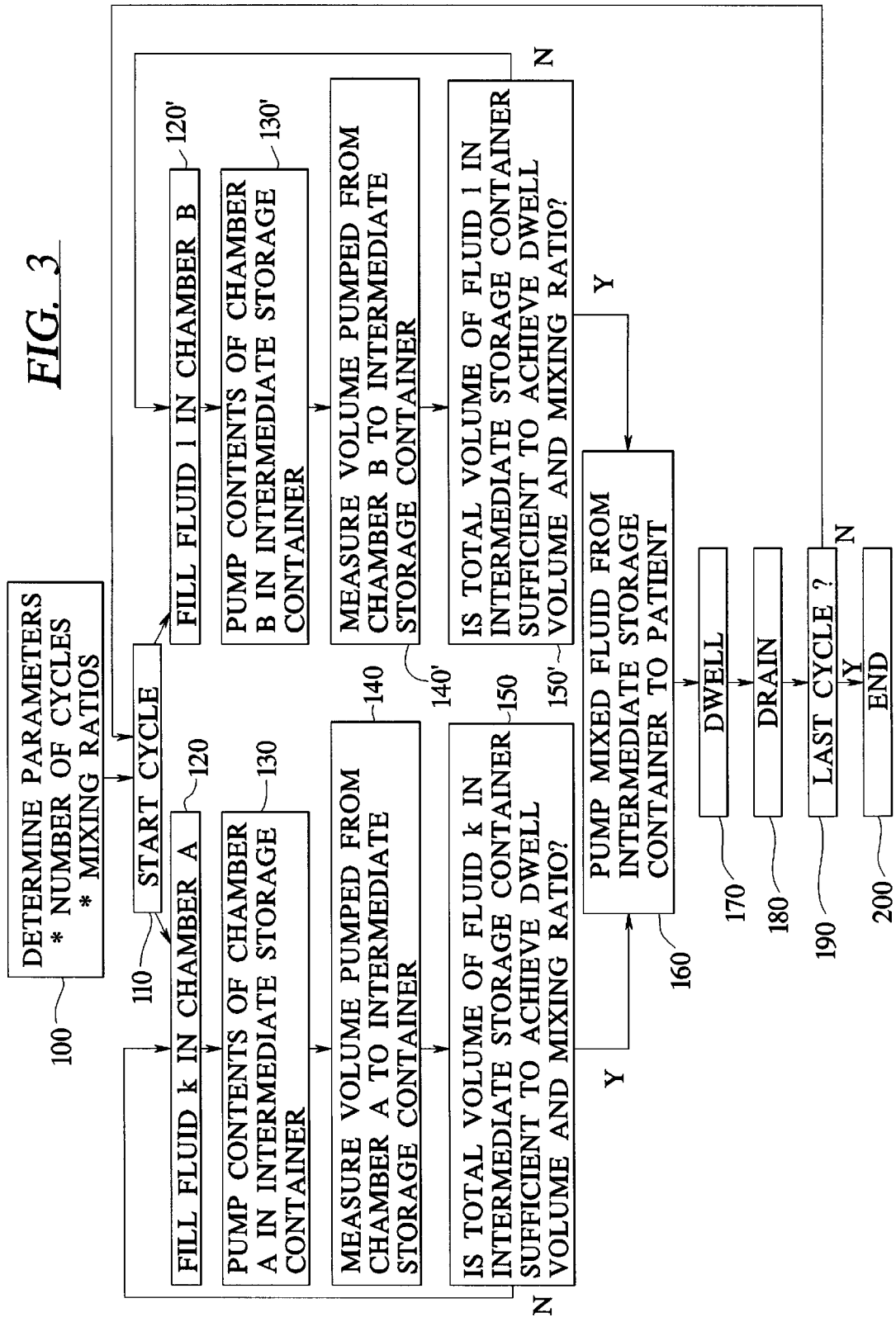
FIG. 3 illustrates a flow diagram for mixing components of a solution with intermediate storage of the solution prior to delivery of the solution to a patient.

The first option is illustrated in FIG. 3 as a flow diagram for active mixing. The method allows preparation of a predetermined quantity of solution (the dwell volume) that may be mixed according to a predetermined ratio of solutions. To this end, parameters are determined and input into the system at step 100. The parameters include the number of cycles to be performed in the treatment along with the mixing ratios of solutions from the various containers.

The START cycle is initiated at step 110 by filling a first fluid in a first container and filling a second fluid in a second container as designated at steps 120 and 120'. Then, at steps 130 and 130', the contents of the first and second containers are pumped to a common intermediate storage container. Simultaneously with pumping of the contents of the containers, the volume pumped is measured from the containers as designated at steps 140 and 140'. Subsequently, at steps 150 and 150', a determination is made as to whether total volume of each of the fluids in the intermediate storage container is sufficient to achieve dwell volume and mixing ratio. An affirmative answer moves to step 160 and begins pumping of the mixed fluid from the intermediate storage container to a patient.

If one or both volumes of fluid are insufficient to achieve the desired and necessary dwell volume and mixing ratio, the process returns to steps 120 and/or 120'. After mixed fluid is pumped from an intermediate storage container to a patient, a dwell step and a drain step are performed as indicated at steps 170 and 180 to complete the cycle. A determination is made at step 190 as to whether the total number of cycles has been completed. If not, a new cycle is started as designated at step 110. Alternatively, if all cycles are completed, the dialysis treatment is completed.

It should be understood that each of the fills need not necessarily have the same mixing ratio. For example, a fill could start with a 1:1 ratio and gradually change to a 2:1 ratio due to the fluid concentration within, for example, the blood stream changing during therapy. Further, the last bag fill for a wet day may, likewise, be of a different mixing ratio.

Figure 5:
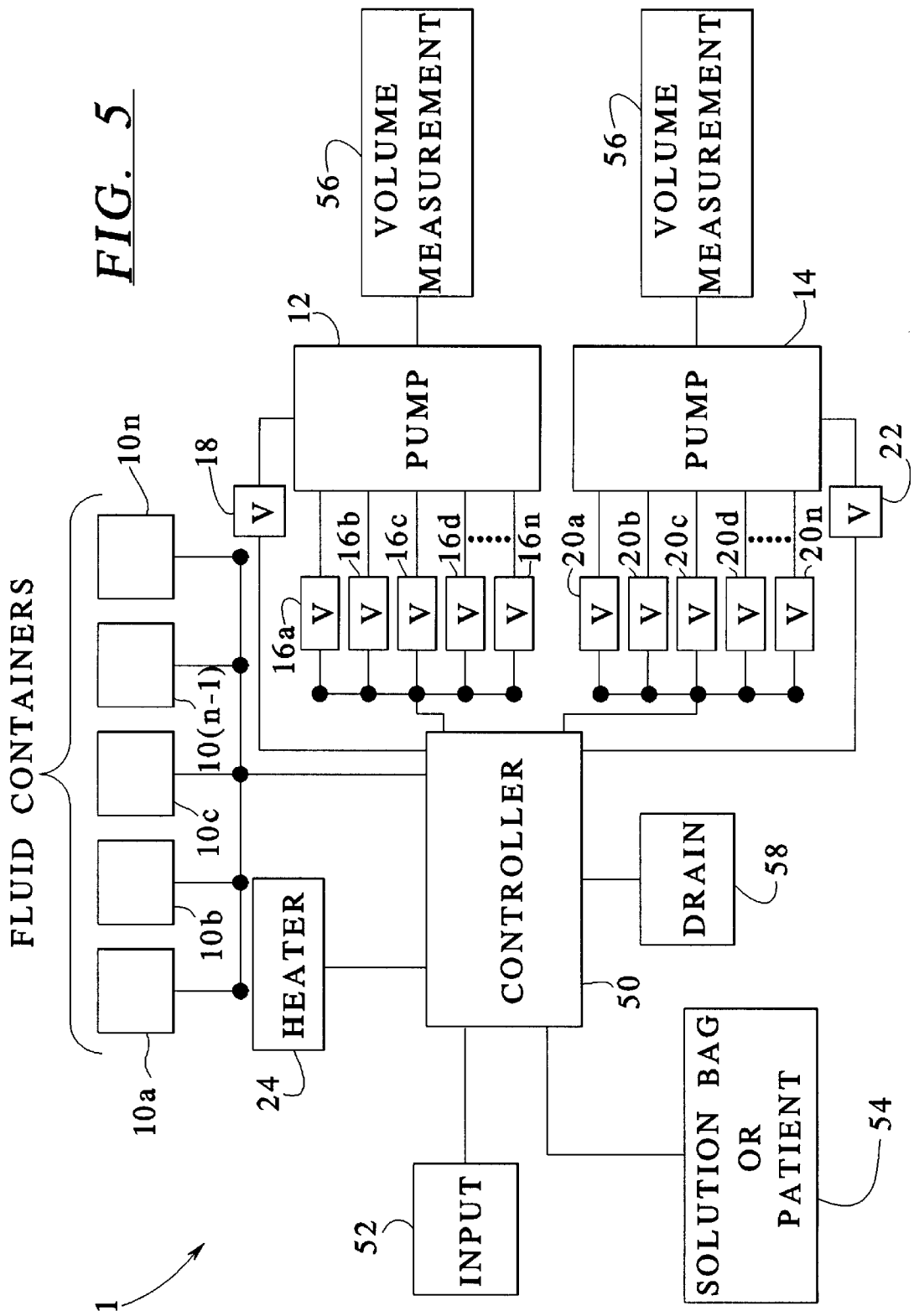
FIG. 5 illustrates a black box diagram of components of an embodiment of a system of the present invention.

To implement the steps delineated in FIG. 3, a program module with pump and valve instructions are provided in a controller or processor as shown in FIG. 5. To fill fluid in a first pumping chamber, all valves are first closed. A supply valve is opened and a negative pressure is applied to the pump chamber. Following filling of the chamber, the supply valve is closed.

To pump the contents of a pumping chamber to an intermediate storage container, all valves are first closed and then the appropriate supply valve is opened and positive pressure is applied to the chamber. When the pumping chamber is emptied, the supply valve is closed.

Of course, other pumping systems may be implemented by those skilled in the art including, but not limited to, peristaltic pumps, bags placed in pressurized or evacuated chambers and the like. Similarly, other volume measuring systems may be employed, such as load cells or simple counting of the revolutions of a peristaltic pump. As an example, multiple bags placed on a single scale could be implemented to monitor fill/drain volumes, Peristaltic pump revolutions or pump strokes could be used to produce the desired mixing ratio. Real time variable mixing is accommodated as a result.

To pump mixed fluid from the intermediate storage container to a patient, all valves are first closed, and a supply valve is opened and negative pressure is applied to a first chamber. The first supply valve is then closed, and a first pumping valve is opened. Positive pressure is applied to the first pumping chamber, and then the pumping valve is closed. This process is repeated unless the intermediate storage container is empty or until the dwell volume is reached.

To drain fluid from the peritoneal cavity, all valves are first closed, and a pumping valve is opened. Negative pressure is applied to a first chamber and then the valve is closed. The drain valve is then open and positive pressure is applied to the chamber. The valve is then closed and the process is repeated unless the peritoneal cavity is empty.

In addition to the foregoing, additional instructions and program modules may be provided including check routines, measurement routines and calculation routines.

Figure 4:
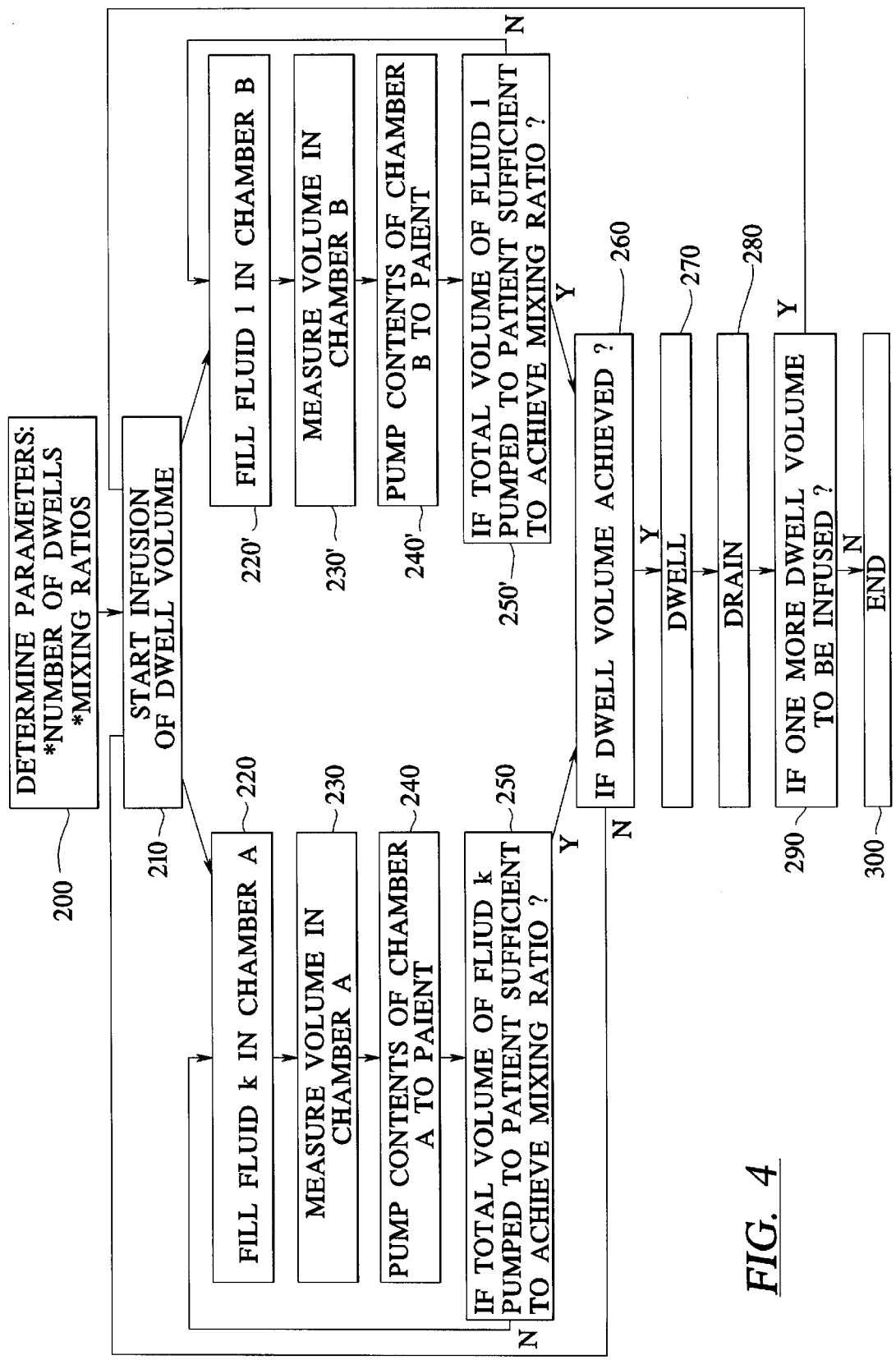
FIG. 4 illustrates a flow diagram for direct infusion of different solutions to a patient.

Referring now to FIG. 4, a method for direct infusion of fluids is shown. The cycle illustrated allows for direct infusion of fluids from different solution containers according to a predetermined ratio. A first step 200 determines parameters including the number of dwells and the mixing ratios required. Infusion of dwell volume is started as shown at step 210.

To begin the infusion, fluids are filled in respective chambers as designated at steps 220 and 220'. Volume is subsequently measured at steps 230 and 230' in each of the respective chambers. The contents of each chamber may be pumped to the patient as designated at steps 240 and 240'. A determination is made at steps 250 and 250' as to whether total volume of each fluid pumped to the patient is sufficient to achieve a predetermined mixing ratio. If both fluids have been pumped to the patient to satisfy the mixing ratio, a determination must be made as to whether the dwell volume has been achieved as indicated at step 260. If so, the dwell and drain steps at steps 270 and 280, respectively, are performed. If another dwell volume is required to be infused as determined at step 290, the system returns to beginning of infusion of dwell volume. If not, the system is ended as designated at step 300.

If, however, insufficient amounts of either or both of the fluids has been pumped, the system returns to steps 220 and/or 220' for filling fluids in the chambers until the mixing ratio is satisfied. If the dwell volume is not satisfactorily achieved as determined at step 260, the infusion of the dwell volume is re-started at step 210.

For simultaneous infusion of different fluids with direct infusion of a first fluid and a 50:50 fluid mix ratio of two fluids, the chamber is filled with a minimal quantity of a first fluid, and a second chamber is filled with a minimal quantity of a second fluid. The fluids are pumped simultaneously from their respective chambers to a patient.

Sequential infusion of different fluids may also be performed by direct infusion of a 50:50 ratio of two fluids. First, a chamber is filled with a minimal quantity of a first fluid, and the first fluid is pumped from the first chamber to the patient. Then, a second chamber is filled with a minimal quantity of a second fluid. The second fluid in the second chamber is pumped to the patient. In the alternative, the same chamber may be used for pumping each of the fluids therein.

In addition to the foregoing, direct infusion having a mixing ratio of, for example, one-third of a first fluid and two-thirds of a second fluid may follow a cycle that begins by filling a first chamber with a second fluid and a minimal quantity pump volume pumping the fluid to a patient. A second chamber is then filled with a first fluid and a minimal quantity pump volume pumps the first fluid to the patient. Then, the second fluid is filled in a third chamber, and a minimal quantity pump volume pumps the fluid to the patient. In an alternative embodiment to that described, the first, second and third chambers may be replaced by a single chamber or a pair of chambers.

Referring now to FIG. 5, a black box diagram of an embodiment of the system 1 is illustrated. As shown, a plurality of fluid containers 10a, 10b, 10c ... 10(n−1), 10n is operatively connected via a controller 50 to the pumps or pump chambers. An input means 52 allows a user to designate specific mixing ratios and/or quantities of fluids to be mixed for administration to a patient. The pumps or pump chamber 12 and 14 via the valves 16a ... 16n and 20a ... 20n, respectively, withdraw fluids from the containers 10a ... 10n as set forth above with reference to FIGS. 3 and 4. And, as previously set forth, the withdrawn fluids from the containers 10a ... 10n may be mixed intermediately in a solution bag as designated at 54 before infusion into a patient or may be infused directly into a patient.

Sensors 56 for measuring volume to the solution bag or patient may be provided to monitor the specific amounts of fluid being delivered. The sensors 56 may feed back signals to the controller 50, or, alternatively, may display volume measurements such that a user may vary the delivery of fluids to be pumped to the solution bag or patient 54. The controller 50 may also control the operation of the valves 18 and 22 for draining of the system 1 by the pumps 12 and/or 14 to the drain 58.

Figure 6:
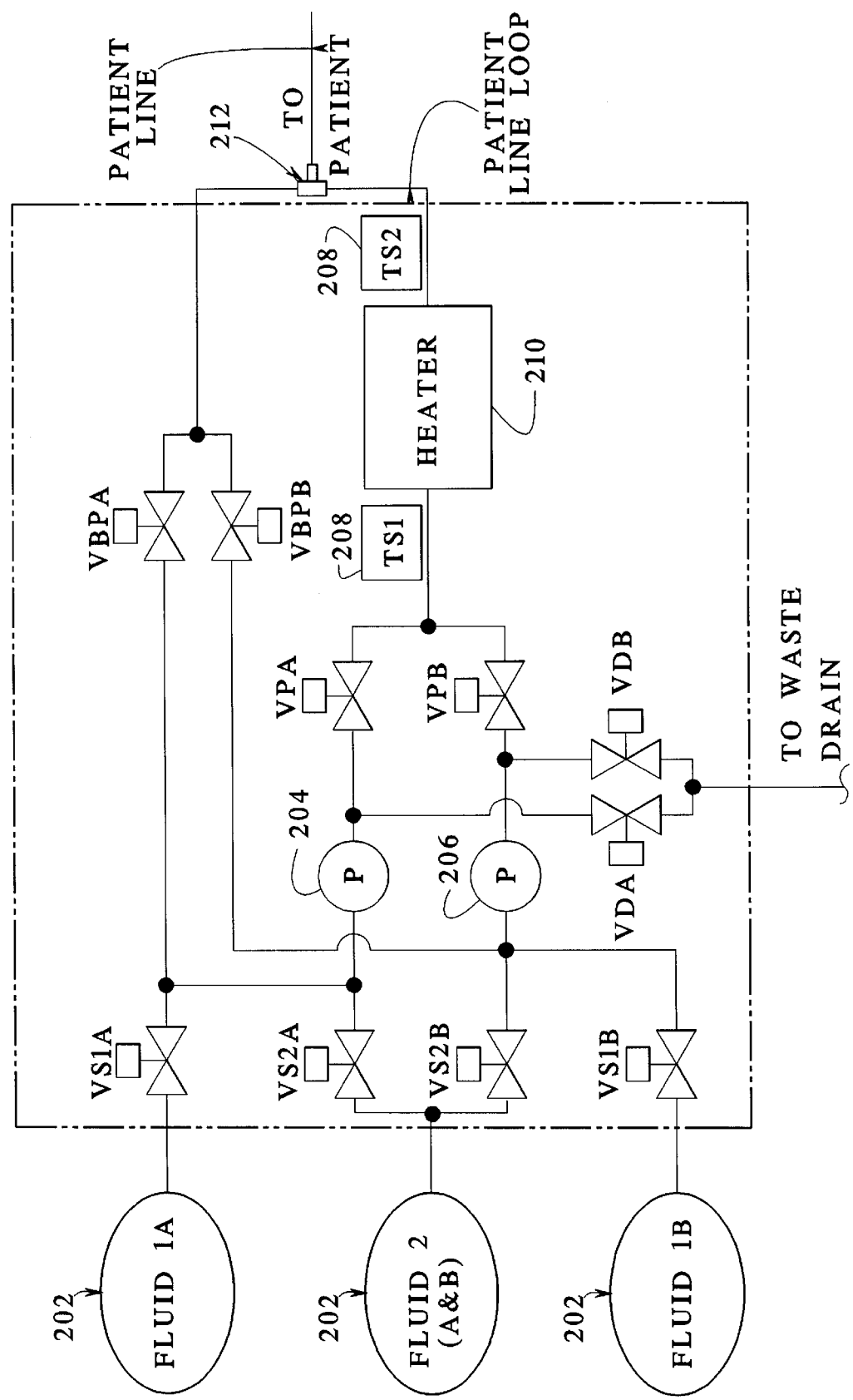
FIG. 6 illustrates a schematic diagram of an embodiment for mixing and/or heating of three solutions and/or components.
Figure 7:
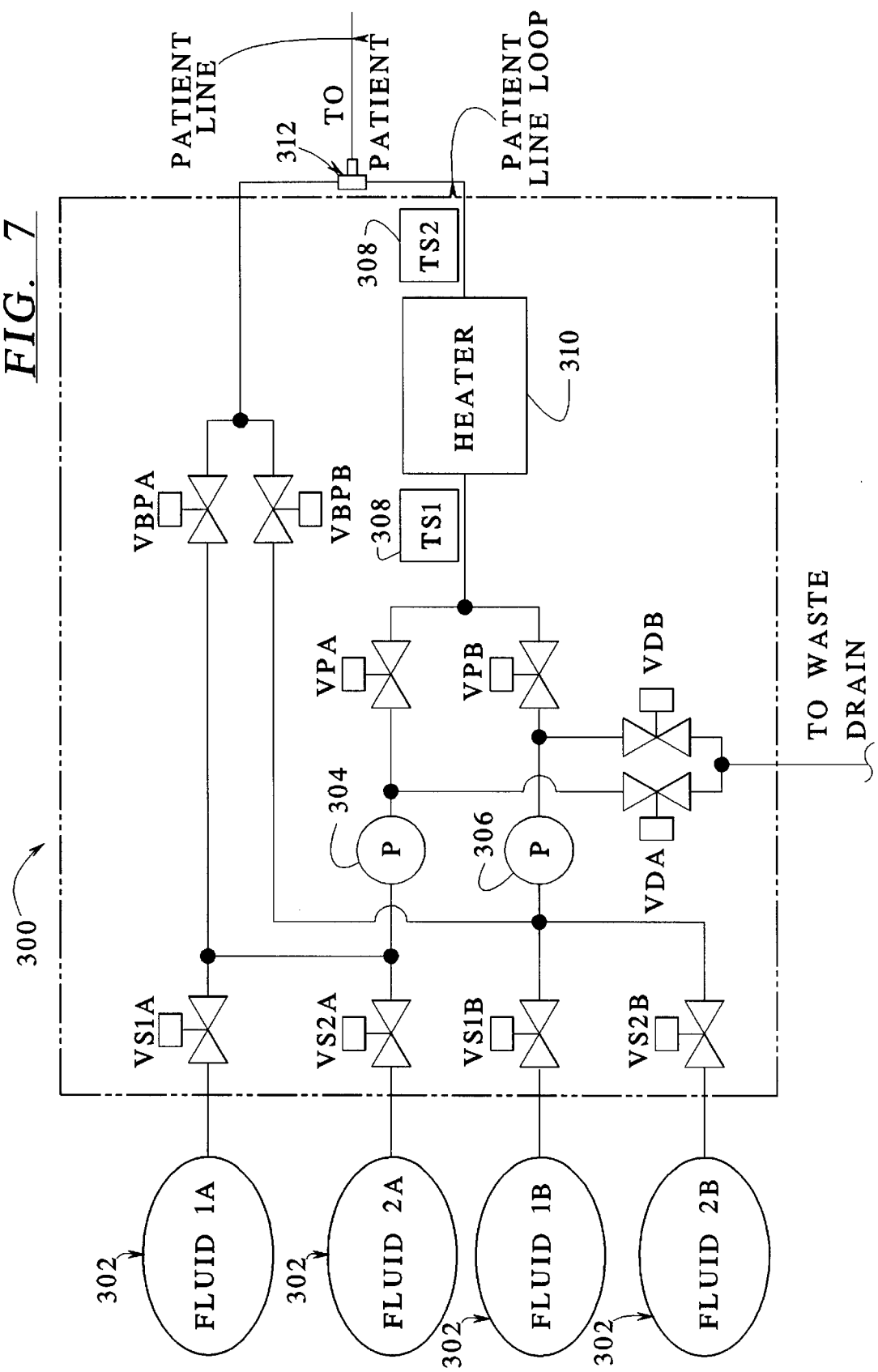
FIG. 7 illustrates a schematic diagram of an embodiment for mixing and/or heating of four solutions and/or components.

Referring now to FIGS. 6 and 7, schematic diagrams of systems 200 and 300, respectively, are illustrated The system 200 illustrated in FIG. 6 achieves active mixing as well as on-line heating for three separate fluid containers 202. Supply valves VS1A, VS2A, VS1B, and VS2B may be used to selectively connect pump 204 and pump 206 to the fluid containers 202. Temperature sensors 208 are implemented to monitor and control temperature of the fluid pumped through a heater 210. The heater 210 may be any known type of heater, such as microwaves, infrared, or the like.

Fluid may be delivered to a patient when the pumps 204, 206 are withdrawing fluid from any of the containers 202 and further when the valves VPA and VPB are open and bypass valves VBPA and VBPB are closed. The bypass valves VBPA and VBPB are open if fluid temperature is not within specific temperature delivery limits. As a result, the fluid is recirculated. Additional heat may be added if the fluid is too cold. On the other hand, if the fluid is too warm, the fluid is simply recirculated until the fluid cools down. Partial recirculation and/or draining may also be accomplished by either drain valve VDA or VDB. This results in more rapid cooling of the temperature of the fluid.

Pumps 204 and 206 may withdraw fluid from the patient, as well, and discharge the fluid to the waste drain whenever the drain valves VDA and VDB and the VBPA and VBPB are open if the other valves are closed. A loop to the patient line as shown in FIG. 6 can be any desired length since the loop can be purged after a drain so that fresh dialysate will be delivered to the patient during all of the next fill. A Venturi tee 212 prevents delivery of fluid to, or withdrawal of fluid from, the patient whenever fluid is passed through the tee 212. This loop is particularly beneficial for pediatric patients wherein a small recirculated volume of fluid can adversely affect the efficacy of dialysis.

FIG. 7 is identical to FIG. 6 except four separate containers 302 are provided containing fluids for active mixing and on-line heating thereof. Two pumps 304,306 are selectively connected to the fluid containers 302 via supply valves VS1A, VS2A, VS1B and VS2B. Temperature sensors 308 are provided to monitor and control the temperature of the fluid pumped through a heater 210. The heater, like that described with reference to FIG. 6, may be any known type, such as microwave, infrared or the like. The remaining valves and Venturi tee 312 operate identically as described with reference to FIG. 60.

The following illustrative examples are offered to describe the advantages of the present invention and should not be deemed as limiting the types of solutions and/or component that may be mixed:

EXAMPLE 1

One container is filled with a solution of dextrose (7.72%), calcium chloride (2.50 mM), magnesium chloride (0.50 mM).

Another container is filled with a solution of sodium bicarbonate (74 mM), sodium chloride (190 mM), pH 7.2. By mixing the solutions (1:1) according to the system described, a solution with dextrose (3.86%), calcium chloride (1.25 mM), magnesium chloride (0.25 mM), sodium chloride (95 mM), sodium bicarbonate (37 mM), pH 7.2 is obtained.

EXAMPLE 2

One container is filled with a solution of dextrose (5.79%).

Another container is filled with a solution of sodium lactate (120 mM), sodium chloride (276 mM), calcium chloride (3.75 mM), magnesium chloride (0.75 mM), pH 6.3.

By mixing the solutions (2:1) according to the system described, a solution with dextrose (3.86%), calcium chloride (1.25 mM), magnesium chloride (0.25 mM), sodium chloride (92 mM), and sodium lactate (40 mM), pH 6.1 is obtained,

EXAMPLE 3

One container is filled with a solution of 8.50% dextrose, calcium chloride (2.50 mM), magnesium chloride (0.50 mM).

A second container is filled with a solution of 2.72% dextrose, calcium chloride (2.50 mM)), magnesium chloride (0.50 mM).

A third container is filled with a solution of sodium chloride (194 mM) and sodium bicarbonate (70 mM), pH 7.2.

By mixing the solutions as described, a final solution can be obtained with calcium chloride (1.25 mM), magnesium chloride (0.25 mM), sodium chloride (97 mM), sodium bicarbonate (35 mM) and dextrose, pH 7.2, and the dextrose concentration can be varied over the therapy session between 1.36% and 4.25%. The dextrose concentration will be 1.36% when the rate of withdrawal from container two and three is equal, and no fluid is being withdrawn from container one. As less fluid is withdrawn from container one and instead drawn from container two, the dextrose concentration will increase. The dextrose concentration will be 4.25% when rate of withdrawal from container one and three is equal, and no fluid is being withdrawn from container two.

EXAMPLE 4

One container is filled with a solution of 8.50% dextrose, calcium chloride, (2.50 mM) magnesium chloride (0.50 mM).

A second container is filled with a solution of 1.00% dextrose, calcium chloride (2.50 mM), magnesium chloride (0.50 mM).

A third container is filled with a solution of sodium chloride (194 mM) and sodium lactate (70 mM), pH 6.3.

By mixing the solutions as described, a final solution can be obtained with calcium chloride (1.25 mM), magnesium chloride (0.25 mM), sodium chloride (97 mM), sodium lactate (35 mM) and dextrose, pH 6.1, and the dextrose concentration can be varied over the therapy session between 0.50% and 4.25%. The dextrose concentration will be 0.50% when the rate of withdrawal from container two and three is equal, and no fluid is being withdrawn from container one. As less fluid is withdrawn from container one and instead drawn from container two, the dextrose concentration will increase. The dextrose concentration will be 4.25% when the rate of withdrawal from container one and three is equal, and no fluid is being withdrawn from container two.

EXAMPLE 5

One container is filled with a solution of glucose polymers (15%), calcium chloride (2.50 mM), magnesium chloride (0.50 mM).

Another container is filled with a solution of amino acids (2%), sodium bicarbonate (74 mM), sodium chloride (126 mM), pH 7.2. By mixing the solutions (1:1) according to the system described, a solution with glucose polymers (7.5%), amino acids (1%), calcium chloride (1.25 mM), magnesium chloride (0.25 mM), sodium chloride (63 mM), sodium bicarbonate (37 mM), pH 7.2 is obtained.

The system and method of the present invention may be used in a variety of situations, not limited to that described above where solutions are mixed and delivered to a patient. For example, the system may be implemented for pre-therapy mixing where one container is attached to a heater line and another container is attached to a supply line. Prior to initiation of therapy, the system performs a mixing procedure. Such a procedure may take hours and typically pulls a portion of the mixture during each pass.

Another option for the system is to provide an empty container on the heater and a first container on a supply line and a second container on the last bag line. During a dwell period, solution may be pulled in equal amounts to the heater bag where the solution would be heated. A Y-junction may be added to the last bag line to allow a manual addition of a different solution to the last bag as required. A patient may manually open a clamp prior to receiving solution from the last bag.

Yet another option is to attach a container to a heater line and another container to a supply line. A second heater may be wrapped around a supply container. During therapy, the system may alternately pull solution from each bag and push a mixture to the patient.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A system for mixing a solution for delivery to a peritoneal cavity of a patient, the system comprising:
   a first container holding a first fluid;
   a second container holding a second fluid;
   means for automatically mixing the first fluid and the second fluid to form the solution wherein the first fluid and the second fluid are independently withdrawn from the first container and the second container, respectively wherein the means for automatically mixing includes a first pumping means and a second pumping means, the first pumping means being connected a first supply valve, the first supply valve being connected to both the first container and a second supply valve, the second supply valve being connected to both the first container and the second pumping means, the second pumping means also being connected to a third supply valve, the third supply valve being connected to both the second container and a fourth supply valve, the fourth supply valve being connected to both the second container and the second pumping means; and
   the first and second pumping means being connected to means for directly delivering the solution to the peritoneal cavity of the patient from the means for automatically mixing.

2. The system of claim 1 further comprising:
   a control means monitoring the solution delivered to the peritoneal cavity of the patient.

3. The system of claim 1 further comprising:
   means for heating the solution prior to delivery to the peritoneal cavity of the patient.

4. The system of claim 1 wherein the means for mixing includes a pumping means.

5. The system of claim 1 wherein the means for automatically mixing includes a microprocessor.

6. The system of claim 2 wherein the control means controls volume of the solution delivered to the peritoneal cavity of the patient.

7. The system of claim 1 wherein the first fluid and the second fluid are sterile.

8. A method for mixing fluids during delivery to a peritoneal cavity of a patient, the method comprising the steps of:
   providing a first container holding a first fluid;
   providing a second container holding a second fluid;
   connecting the first container to a first pumping means and a second pumping means such that either pumping means may pump fluid from said first container;
   such that either pumping means may pump fluid from said first container connecting the second container to the first pumping means and the second pumping means;

connecting the first and second pumping means to an intermediate container;

automatically withdrawing the first fluid and the second fluid from their respective containers with the first and second pumping means sequentially or simultaneously and pumping the first fluid and second fluid to the intermediate container;

mixing the first fluid and the second fluid forming a mixed solution in the intermediate container; and directly delivering the mixed solution from the intermediate container to the peritoneal cavity of the patient following mixing.

9. The method of claim 8 further comprising the step of:

controlling volume of withdrawal of the first fluid and the second fluid independently.

10. The method of claim 8 further comprising the step of:

controlling volume of delivery of the mixed solution to the peritoneal cavity of the patient.

11. The method of claim 8 further comprising the step of:

heating the mixed solution prior to delivery to the peritoneal cavity of the patient.

12. The method of claim 8 wherein the patient is undergoing peritoneal dialysis.

13. A method for direct infusion of a plurality of fluids to a peritoneal cavity of a patient, the method comprising the steps of:

providing at least two containers including a first container and a second container;

filling the first container with a first one of the plurality of fluids;

directly pumping the first one of the plurality of fluids to the peritoneal cavity of the patient with one of a first pumping means or a second pumping means;

filling the second container with a second one of the plurality of fluids; and directly pumping the second one of the plurality of fluids to the peritoneal cavity of the patient with one of the first pumping means or the second pumping means.

14. The method of claim 13 further comprising the step of:

inputting an amount of each of the plurality of fluids to be pumped to the peritoneal cavity of the patient.

15. A method for infusion of a plurality of fluids to a peritoneal cavity of a patient, the method comprising the steps of:

providing a plurality of containers equal to the plurality of fluids;

directly pumping each of the plurality of fluids from each of the plurality of containers sequentially or simultaneously with one of a first pumping means or a second pumping means to the peritoneal cavity of the patient or a storage means prior to delivery to the peritoneal cavity of the patient, the first and second pumping means each being connected to each of the plurality of containers such that wither pumping means may pump fluid from at least one of said containers.

16. The method of claim 15 further comprising the step of:

inputting an amount of each of the plurality of fluids to be pumped to the peritoneal cavity of the patient.

17. A system for infusion of a plurality of solutions to a peritoneal cavity of the patient, the system comprising:

means for storing each of the plurality of solutions in a plurality of separate containers;

input means for inputting an amount of each of the plurality of solutions required for delivery to the peritoneal cavity of the patient; and pumping means for pumping each of the plurality of solutions directly to the peritoneal cavity of the patient including first and second pumping means each being connected to each of the plurality of containers in such a manner that either pumping means may be used to pump fluid from at least on of said containers.

18. The system of claim 17 wherein the first and second pumping means simultaneously pump each of the solutions to the peritoneal cavity of the patient.

19. The system of claim 17 wherein the pumping means sequentially pumps each of the solutions to the peritoneal cavity of the patient.

20. The system of claim 17 wherein the pumping means alternately pumps each of the solutions to the peritoneal cavity of the patient.

21. The system of claim 17 further comprising:

storage means receiving each of the plurality of solutions for mixing prior to delivery to the peritoneal cavity of the patient.

22. The system of claim 17 further comprising:

control means operatively connected to the pumping means and capable of controlling the pumping means for sequential or simultaneous delivery of the solution.

23. The system of claim 17 further comprising:

means for heating at least one of the plurality of solutions.

24. The system of claim 17 wherein the input means and pumping means are capable of receiving and pumping variable mixing ratios of the plurality of solutions.

25. The system of claim 17 wherein the pumping means alters the amount of each of the plurality of solutions between fills.

* * * * *

UNITED STATES PATENT AND TRADEMARK OFFICE
CERTIFICATE OF CORRECTION

PATENT NO. : 5,925,011
DATED : July 20, 1999
INVENTOR(S) : Dirk Faict, et al.

It is certified that error appears in the above-identified patent and that said Letters Patent is hereby corrected as shown below:

Column 8, Line 23: delete "60" and insert --6--

Column 12, Line 6: delete "wither" and insert --either--

Column 12, Line 25: delete "on" and insert --one--

Signed and Sealed this

Eleventh Day of April, 2000

Attest:

Attesting Officer

Q. TODD DICKINSON

Director of Patents and Trademarks